(12) United States Patent
Spencer et al.

(10) Patent No.: US 11,083,399 B2
(45) Date of Patent: *Aug. 10, 2021

(54) ELECTRODE PATCH FOR HEALTH MONITORING

(71) Applicant: InfoBionic, Inc., Lowell, MA (US)

(72) Inventors: Darren Spencer, Fewcott (GB); Peter Van Der Sluis, Laguna Beach, CA (US)

(73) Assignee: InfoBionic, Inc., Lowell, MA (US)

( * ) Notice: Subject to any disclaimer, the term of this patent is extended or adjusted under 35 U.S.C. 154(b) by 49 days.

This patent is subject to a terminal disclaimer.

(21) Appl. No.: 16/409,951

(22) Filed: May 13, 2019

(65) Prior Publication Data

US 2019/0320929 A1  Oct. 24, 2019

Related U.S. Application Data

(63) Continuation of application No. 15/278,527, filed on Sep. 28, 2016, now Pat. No. 10,327,657.

(60) Provisional application No. 62/237,188, filed on Oct. 5, 2015.

(51) Int. Cl.
*A61B 5/259* (2021.01)
*A61B 5/282* (2021.01)
*A61B 5/332* (2021.01)
*A61B 5/00* (2006.01)
*A61B 5/339* (2021.01)

(52) U.S. Cl.
CPC ............ *A61B 5/259* (2021.01); *A61B 5/0006* (2013.01); *A61B 5/282* (2021.01); *A61B 5/332* (2021.01); *A61B 5/6823* (2013.01); *A61B 5/339* (2021.01)

(58) Field of Classification Search
None
See application file for complete search history.

(56) References Cited

U.S. PATENT DOCUMENTS

| | | | |
|---|---|---|---|
| 3,792,700 A | 2/1974 | Sarnoff et al. | |
| 4,004,577 A | 1/1977 | Sarnoff | |
| 6,339,720 B1 | 1/2002 | Anzellini et al. | |
| 8,280,481 B2 * | 10/2012 | Copp | A61B 5/259 600/396 |
| 9,155,484 B2 | 10/2015 | Baker et al. | |
| 9,237,848 B2 | 1/2016 | Russell | |
| 9,700,222 B2 | 7/2017 | Quinlan et al. | |
| 2014/0206976 A1 | 7/2014 | Thompson et al. | |
| 2014/0330136 A1 | 11/2014 | Manicka et al. | |
| 2015/0094557 A1 * | 4/2015 | Hsu | A61B 5/282 600/391 |
| 2015/0126844 A1 | 5/2015 | Yang et al. | |
| 2015/0148637 A1 | 5/2015 | Golda et al. | |

(Continued)

*Primary Examiner* — Brian T Gedeon
(74) *Attorney, Agent, or Firm* — Bookoff McAndrews, PLLC

(57) ABSTRACT

A method of measuring bioelectric signals of a patient having an axis extending from the patient's head to the patient's feet includes attaching a patch to the patient's skin. The patch may include a first electrode and a second electrode spaced apart along a longitudinal axis of the patch. The patch may be attached such that the longitudinal axis of the patch is generally aligned with the axis of the patient. The method may also include attaching a third electrode to the patient's skin, and measuring bioelectric signals of the patient using the first electrode, the second electrode, and the third electrode.

8 Claims, 4 Drawing Sheets

(56) References Cited

U.S. PATENT DOCUMENTS

| | | |
|---|---|---|
| 2016/0279405 A1 | 9/2016 | Riley et al. |
| 2016/0296171 A1 | 10/2016 | Drori et al. |
| 2016/0302681 A1* | 10/2016 | Levant ................. A61B 5/0006 |
| 2017/0303815 A1* | 10/2017 | De Limon ............ A61B 5/4878 |
| 2018/0172520 A1* | 6/2018 | Jang ....................... G01K 13/20 |

* cited by examiner

ELECTRODE PATCH FOR HEALTH MONITORING

CROSS-REFERENCE TO RELATED APPLICATIONS

This application is a continuation of U.S. application Ser. No. 15/278,527, filed Sep. 28, 2016, which claims the benefit of priority from U.S. Provisional Application No. 62/237,118, filed on Oct. 5, 2015, the disclosure of each of which is incorporated by reference herein in its entirety.

TECHNICAL FIELD

Various embodiments of the present disclosure relate to an electrode patch and systems and methods of using an electrode patch for health monitoring, and more particularly, to an electrode patch and systems and methods of using an electrode patch for physiologic data monitoring.

BACKGROUND

Physiologic data may be used to monitor the health of a patient. For example, bioelectric signals (e.g., electrocardiogram or ECG signals) from the patient's heart may be used to monitor cardiac health. ECG is a recording of the electrical activity of the heart. During ECG monitoring, electrodes attached to a patient's skin are used to detect electrical activity of the heart over a period of time. During ECG monitoring, electrical impulses generated by the heart during each heartbeat are detected and recorded and/or displayed on a device. Analysis of the data reveals the cardiac health (e.g., rate and regularity of heartbeats, size and position of the chambers, the presence of any damage to the heart, effects of drugs or devices used to regulate the heart, etc.) of the patient.

Multiple electrodes (e.g., left arm (LA), right arm (RA), and left leg (LL) electrodes) may be attached to the patient's skin for ECG measurement. These electrodes may be combined into a number of pairs (e.g., three pairs LA-RA, LA-LL, and RA-LL), and voltage signals may be recorded across each pair. Each pair is known as a lead. Each lead looks at the heart from a different angle. Different types of ECG measurements can be referred to by the number of leads that are recorded (e.g., 3-lead, 5-lead, 12-lead ECG, etc.).

Many cardiac problems become noticeable only during physical activity (walking, exercise, etc.). An ambulatory electrocardiogram (ECG) continuously monitors the electrical activity of the heart while a patient does normal activities. Typically, a 12-lead or a 5-lead ECG is used for periodic ECG monitoring (e.g., at a doctor's office, etc.) and a 3-lead ECG is used for continuous ambulatory monitoring. In 3-lead monitoring, ECG data is collected using three electrodes attached to the patient. The collected data is recorded in a monitor operatively coupled to the electrodes. The stored data is analyzed by a health care provider. In some cases, the monitor may transmit ECG data to a health care provider for analysis. Several types of monitors (e.g., Holter monitor, event monitors, mobile cardiovascular telemetry monitors, etc.) are known in the art. Some of these monitors store the data for subsequent analysis by a health care provider, while others transmit (real-time, periodically, or on demand) the collected ECG data to a remote site where it is analyzed.

Regardless of the type of ECG measurement, the quality of the measurement depends on the attachment quality and positioning of the electrodes on the body. Typically, electrodes are positioned to obtain good signals from all regions of the heart. Organizations such as American Heart Association (AHA) and International Electrotechnical Commission (IEC) provide guidelines for electrode positions for ECG measurements. While these recommended electrode positions result in acceptable ECG data, there remains a need for improved ECG measurement systems and methods.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

SUMMARY

Figure 1:
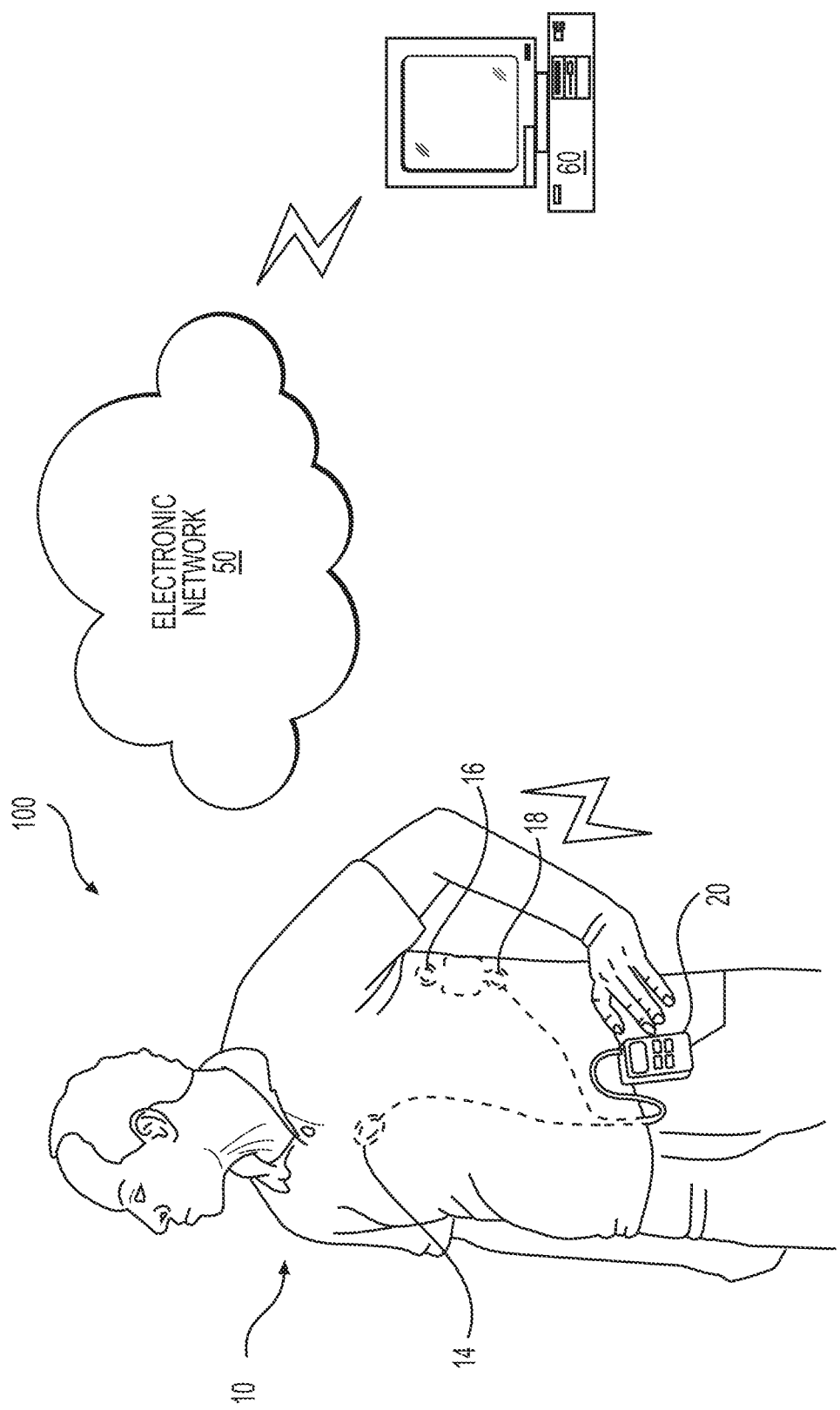
FIG. 1 illustrates an exemplary system for measuring ECG of a patient.

In one aspect, a method of measuring bioelectric signals of a patient having an axis extending from the patient's head to the patient's feet is disclosed. The method may include attaching a patch to the patient's skin. The patch may include a first electrode and a second electrode spaced apart along a longitudinal axis of the patch. The patch may be attached such that the longitudinal axis of the patch is generally aligned with the axis of the patient. The method may also include attaching a third electrode to the patient's skin, and measuring bioelectric signals of the patient using the first electrode, the second electrode, and the third electrode.

Additionally or alternatively, the method may include one or more of the following aspects: the bioelectric signals may include ECG signals; attaching the patch may include attaching the patch under an arm pit of the patient; attaching the third electrode may include attaching the third electrode above the right atrium of the patient's heart; the method may further include electrically connecting the first electrode, the second electrode, and the third electrode to a portable monitor, and using the monitor to measure the bioelectric signals; and attaching the monitor to the patch; attaching the patch to the patient's skin includes attaching the patch to a thoracic region spanning about 15° on either side of a linear axis extending through the patient's outstretched arms.

In another aspect, a method of measuring ECG signals of a patient including an axis extending from the patient's head to the patient's feet, is disclosed. The method may include attaching a patch under the left armpit in the patient's thoracic region. The patch may include a first electrode and a second electrode spaced apart along a longitudinal axis of the patch, the patch being attached such that the longitudinal axis is generally aligned with the axis of the patient. The method may also include attaching a third electrode to a chest of the patient, and measuring ECG signals using the first electrode, the second electrode, and the third electrode.

Additionally or alternatively, the method may include one or more of the following aspects: electrically connecting the first electrode, the second electrode, and the third electrode to a portable monitor, and using the monitor to measure the ECG signals; further include attaching the monitor to the patch; the monitor is attached to the patch between the first electrode and the second electrode; attaching the patch includes attaching the patch to a thoracic region spanning about 15° on either side of a linear axis extending through the patient's outstretched arms; electrically connecting the third electrode to the portable monitor includes directing measured signals from the third electrode to the patch; wherein the patch includes an adhesive layer on a surface covered by a protective strip, and the method further includes removing the protective strip prior to attaching the patch.

In another aspect, an adhesive electrode patch for measuring bioelectric signals from a patient is disclosed. The patch may include an elongated flexible strip extending along a longitudinal axis from a first end region to a second end region. The patch may also include a first electrode on the first end region, and a second electrode on the second end region; and a central region located between the first end region and the second end region. A width of the central region in a direction transverse to the longitudinal axis is greater that a width of the first and second end regions.

Additionally or alternatively, the patch may include one or more of the following aspects: a skin-facing surface and an exposed surface opposite the skin-facing surface, the skin-facing surface may include an adhesive layer covered by a protective strip; the exposed surface of the strip may include markings to assist a patient in aligning the strip on the patient's body; the strip may include conductive traces extending from the first electrode and the second electrode to the central region; and the strip may be made of a fabric material, and the first electrode and second the electrodes include silver.

DETAILED DESCRIPTION

Reference will be made in detail to exemplary embodiments of the disclosure, examples of which are illustrated in the accompanying drawings. Wherever possible, the same reference numbers will be used throughout the drawings to refer to the same or like parts.

Embodiments of the present disclosure may include methods and systems for monitoring physiologic data of a patient. Various aspects of the present disclosure may be used in combination with, or include, one or more features disclosed in U.S. Pat. No. 8,478,418 (issued Jul. 2, 2013) and U.S. Pat. No. 8,620,418 (issued Dec. 31, 2013), each of which are incorporated by reference herein in their entireties. While an exemplary embodiment of measuring ECG data is described below, it should be noted that, the current disclosure may be applied to the measurement of any physiologic data. For example, the disclosed systems and methods may be used to measure signals indicative of heart rate, activity level (e.g., physical mobility or movement), respiration rate, blood pressure (e.g., systolic and/or diastolic), blood oxygen saturation (SpO2), blood glucose or insulin level, pulse oximetry, impedance, body temperature, etc. It is also contemplated that, in some embodiments, the measured physiologic data may be used to determine a cardiac safety indicator such as QT prolongation, ST elevation, etc.

FIG. 1 is a schematic illustration of an exemplary system 100 for measuring ECG of a patient 10. A plurality of electrodes 14, 16, 18 may be attached to the patient 10 to detect ECG signals. The electrodes 14, 16, 18 detect (and in some cases amplify) tiny electrical changes on the skin that are caused when heart muscles depolarize during each heartbeat. At rest, each heart muscle cell has a negative charge (called the membrane potential) across its cell membrane. Decreasing this negative charge toward zero, via the influx of the positive cations (Na+ and Ca++) is called depolarization. Depolarization activates mechanisms in the cell that cause it to contract. During each heartbeat, a healthy heart will have an orderly progression of a wave of depolarization that is triggered by the cells in the sinoatrial node, spreads out through the atrium, passes through the atrioventricular node and then spreads all over the ventricles. The depolarization wave (or ECG data) is indicative of the overall rhythm of the heart and is detected as variations in voltage between the electrode pairs (e.g., between electrodes 14-16, 14-18, and 16-18).

System 100 may include a monitor 20 operatively coupled to the electrodes 14, 16, 18. Monitor 20 may be adapted to receive and store the ECG data from the electrodes 14, 16, 18. Monitor 20 may be coupled to electrodes 14, 16, 18 wirelessly or using a wired connection. In embodiments where the ECG data is transmitted to monitor 20 wirelessly, some or all of electrodes 14, 16, 18 may include a transceiver to transmit the measured ECG data to monitor 20. In some embodiments, monitor 20 may transfer at least a portion of the measured ECG data to a remote analysis station 60 for analysis. Although analysis station 60 is illustrated as a computer, in general, analysis 60 station may include any collection of computational devices and personnel (e.g., one or more servers, databases, and computers networked together).

The ECG data from monitor 20 may be transferred to remote analysis station 60 over a wired connection, using a portable storage medium (transferable memory device, etc.), or transferred wirelessly over an electronic network 50 (e.g., the internet). Rather than transferring data directly to analysis station 60, in some embodiments, monitor 20 may transfer the data to analysis station 60 through an intermediate device (e.g., cellular phone, PDA, etc.). That is, the ECG data from monitor 20 may be first sent to an intermediate device such as a cellular phone using Bluetooth or other similar technologies (HomeRF, IrDA, etc.), when monitor 20 is close to the cellular phone. The ECG data from the cellular phone may then be sent to the analysis station 60 over the phone's cellular communication network or the electronic network 50.

Analysis station 60 may analyze the ECG data to check the cardiac health of patient 10. Any analysis methodology known in the art may be used to analyze the received data (e.g., a methodology described by Philip de Chazal, et al., in "Automatic Classification of Heartbeats Using ECG Morphology and Heartbeat Interval Features," IEEE Transactions on Biomedical Engineering, Vol. 51, No. 7, July, 2004). Since methods and algorithms for analyzing ECG data are well known in the art, they are not described herein. In some embodiments, monitor 20 may at least partially analyze the collected ECG data before it is transferred to analysis station 60.

In some embodiments, monitor 20 may store the collected ECG data, and continuously transmit (directly or through an intermediate device) a subset of the data (e.g., data at a lower resolution, etc.) to the analysis station 60. The analysis station 60 may analyze the received data to determine if it indicates an anomaly (e.g., an arrhythmia, an unexpected trend in the data, etc.). If an anomaly is indicated, analysis station 60 may request (i.e. transmit instructions) the monitor 20 for more data (e.g., data from the same time frame at a higher resolution, etc.). Upon receipt of this request, the monitor 20 may retrieve the requested data from memory and transmit it to the analysis station 60. The analysis station 60 may then analyze the data (e.g., using a more rigorous analysis methodology) to confirm or refute the anomaly detected during the previous analysis. This analysis methodology is described in more detail in U.S. Pat. No. 8,478,418, which is incorporated by reference herein.

Monitor 20 may be any type of portable monitor known in the art (e.g., Holter monitor, event monitor, mobile cardiovascular telemetry (MCT) monitor, etc.). Monitor 20 may include integrated circuits (microprocessor, memory, communication devices, etc.), visual displays (LED, LCD, etc.), and/or buttons that can be activated by the patient 10. The integrated circuits of monitor 20 may enable processing of collected ECG data, and communication between monitor 20, the intermediate device (if any), and the analysis station 60. The user activatable buttons may enable the patient 10 to trigger an activity (data collection, communication with analysis station 60, etc.) when the patient 10 feels uncomfortable (e.g., experiences chest pains, etc.), and the display may enable the monitor 20 and analysis station 60 to communicate with patient 10 (e.g., using text messages).

Monitor 20 may be a portable device, sized and adapted to be kept in the possession (strapped, attached, placed in the pocket, etc.) of patient 10. Such a portable monitor 20 may enable the patient 10 to go about the patient's daily activities while the monitor 20 records (and/or transfers) ECG data. In the exemplary embodiment illustrated in FIG. 1, monitor 20 is shown as a device attached (e.g., clipped) to the patient's belt. However, this is only exemplary, and other configurations are possible. For example, in some embodiments, monitor 20 may be combined with, or incorporated into a cellular phone (or another device, such as, watch, etc.). In embodiments where electrodes 14, 16, 18 are connected by a wire to the monitor, monitor 20 may include a connector to receive the connecting wire. In embodiments where electrodes 14, 16, 18 are coupled wirelessly, monitor 20 may include a transceiver to communicate with a transceiver of electrodes 14, 16, 18.

Figure 2A:
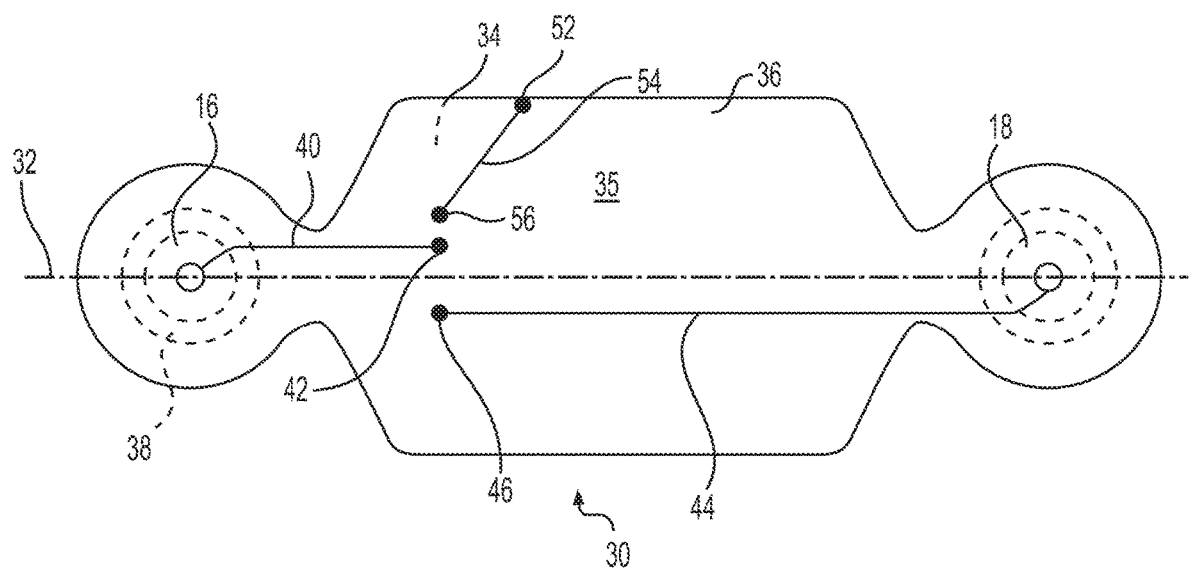
FIGS. 2A and 2B illustrate top and side views respectively of an exemplary adhesive patch used in the ECG measurement system of FIG. 1.
Figure 2B:
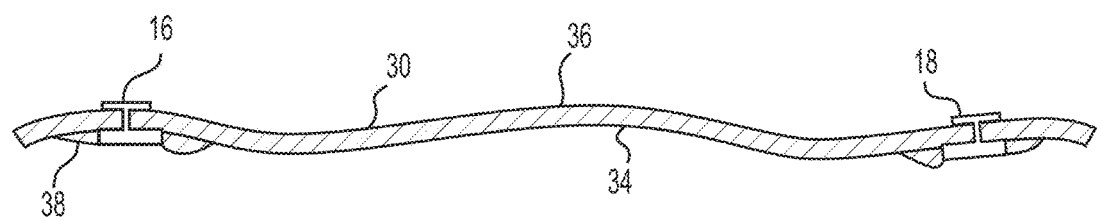

Electrodes 14, 16, 18 may be any type of electrodes that may be attached to the skin of patient 10. In some embodiments, at least two of the electrodes 16, 18 may be configured as an adhesive patch 30. FIGS. 2A and 2B illustrate an exemplary embodiment of an adhesive patch 30. FIG. 2A illustrates a top view of patch 30, and FIG. 2B illustrates its side view. In the description that follows, reference will be made to both FIGS. 2A and 2B. Adhesive patch 30 may be made of a flexible material (tape, fabric, etc.) that is adapted to conform to the contours of the patient's skin. Adhesive patch 30 may be configured as a reusable patch or a disposable patch. In some embodiments, the material of adhesive patch may have pores (or otherwise breathable) or other features to enhance patient comfort. One side (skin-facing side 34) of the adhesive patch 30 may include an adhesive. Any type of adhesive (e.g., acrylates, silicones, hydrogels, hydrocolloids, polyurethanes, etc.) that can attach the adhesive patch 30 to the skin of the patient may be used. In some embodiments, the adhesive may be coated to the skin-facing side 34 of the adhesive patch 10. In some embodiments, the adhesive may be covered by a strip of removable protective material (e.g., similar to adhesive bandages such as Band-Aid). After removing this protective strip, the adhesive patch 30 may be attached on the patient by pressing the skin-facing side 34 to the patient's skin. In this configuration, the side of patch 30 opposite to the skin-facing side (i.e., exposed side 36) is exposed to the atmosphere. Although patch 30 is described as being attached to the patient's skin using an adhesive layer, it is also contemplated that in some embodiments, patch 30 may be attached using other attachment mechanisms (e.g., adhesive tape, sutures, clips, etc.).

In general, adhesive patch 30 may have any size and shape. In some embodiments, adhesive patch 30 may have an elongated shape (e.g., oval, elliptical, rectangular, dumbbell shaped, hour-glass shaped etc.) with an axis (longitudinal axis 32) extending along its length. Electrodes 16, 18 may be spaced apart along the longitudinal axis 32 of adhesive patch 30. In an exemplary embodiment, as illustrated in FIG. 2A, the elongated shape of patch 30 may include circular regions at its two ends, the sides of which converge to form narrower neck regions that further expand to a wider central region 35. In the embodiment of FIG. 2A, electrodes 16, 18 are placed on the circular regions and spaced apart by the wider central region 35. The wider central region 35 and the circular end regions may have any dimensions suitable for its purpose. In some embodiments (see FIG. 2A), the central region 35 may be sized to attach a monitor 20 thereon.

Electrodes 16, 18 may include any material and configuration (size and shape) that are currently used for, or are suitable for, bioelectric measurements. See, Neuman, M. R., Chapter 40: Biopotential Electrodes, "Biopotential Electrodes," The Biomedical Engineering Handbook: Second Edition, Ed. Joseph D. Bronzino, Boca Raton, CRC Press LLC, 2000, which is incorporated by reference herein. In some embodiments, electrodes 16, 18 may have a substantially circular cross-sectional shape and be made of silver with a surface layer of silver chloride. However, other shapes (square, rectangular, polygonal, etc.) are also contemplated. Electrodes 16, 18 may be attached to the adhesive patch 30 in any manner (e.g., adhesives, etc.). In some embodiments, the electrodes 16, 18 may be stitched or weaved into the material of the adhesive patch 30. In some embodiments, the material of electrodes 16, 18 may be deposited or coated on the patch 30. In some embodiments, as illustrated in FIG. 2B, electrodes 16, 18 may have a region of reduced diameter along its thickness (in a direction perpendicular to the plane of the paper), and may be attached to patch 30 like a button.

In some embodiments, adhesive patch 30 may also include an electrically conductive gel 38. The conductive gel 38 may be provided in a region adjacent the electrodes 16, 18. Conductive gel 38 may be a viscous conductive medium that fills any gap between the electrodes 16, 18 and the patient's skin to improve detectability of electrical activity under the skin. Any type of commercial or specially formulated gel known in the art may be used as conductive gel 38.

In some embodiments, conductive patch 30 may include conductive traces 40, 44 that extend from the electrodes 16, 18 to terminals 42, 46 of patch 30. These traces 40, 44 may include any conductive material and may be provided by any known additive and/or subtractive processes (masking and plating/deposition, plating/depositing and etching, etc.). These traces 40, 44 may extend along the skin-facing surface 34 or the exposed surface 36 of patch 30. The conductive traces 40, 44 may direct the measured bioelectric signals from electrodes 16, 18 to the terminals 42, 46. The terminals 42, 46 may be the ends of traces 40, 44 positioned on the exposed surface 36 of the patch 30. In embodiments where the traces 40, 44 extend along the skin-facing surface 34, a through-hole via may electrically connect ends of the traces 40, 44 to the terminals 42, 46. In general, the terminals 42, 46 may be positioned anywhere on patch 30. In some embodiments, the terminals 42, 46 may be positioned on an edge of patch 30. In such embodiments, an external wire attached to (e.g., clipped, etc.) the terminals 42, 46 may retrieve the measured bioelectric signals from the patch 30. In some embodiments, as illustrated in FIG. 2A, the terminals 42, 46 may be positioned on the central region 35 of patch 30. In some such embodiments, patch 30 may also include a trace 54 that extends from a terminal 52 at an edge of the patch 30 to a terminal 56 at the central region 35. An external wire attached to terminal 52 may direct measured signals from electrode 14 to terminal 56. In some such embodiments, a monitor 20 attached to central region 35 may receive the measured signals from terminals 42, 46, and 56.

In some embodiments, adhesive patch 30 may also include circuitry (not shown) to process (amplify, filter, etc.) the bioelectric signals measured by the electrodes 16, 18 (and, in some embodiments, electrode 14). In some embodiments, the circuitry may be formed directly on the material of patch 30 using fabrication techniques known in the art (e.g., using IC fabrication techniques). In some embodiments, the circuitry may be formed on a discrete component (integrated circuit chip, printed circuit board, etc.) which is attached to the patch 30. The circuitry may be positioned anywhere on patch 30. In some embodiments, the circuitry may be positioned on the central region 35 such that the measured signals are processed by the included circuitry on its way from an electrode to its corresponding terminal. In embodiments where the bioelectric signals are wirelessly transmitted to monitor 20, the circuitry may also include a transmitter (or transceiver) circuit to transmit the signals to monitor 20.

Figure 3A:
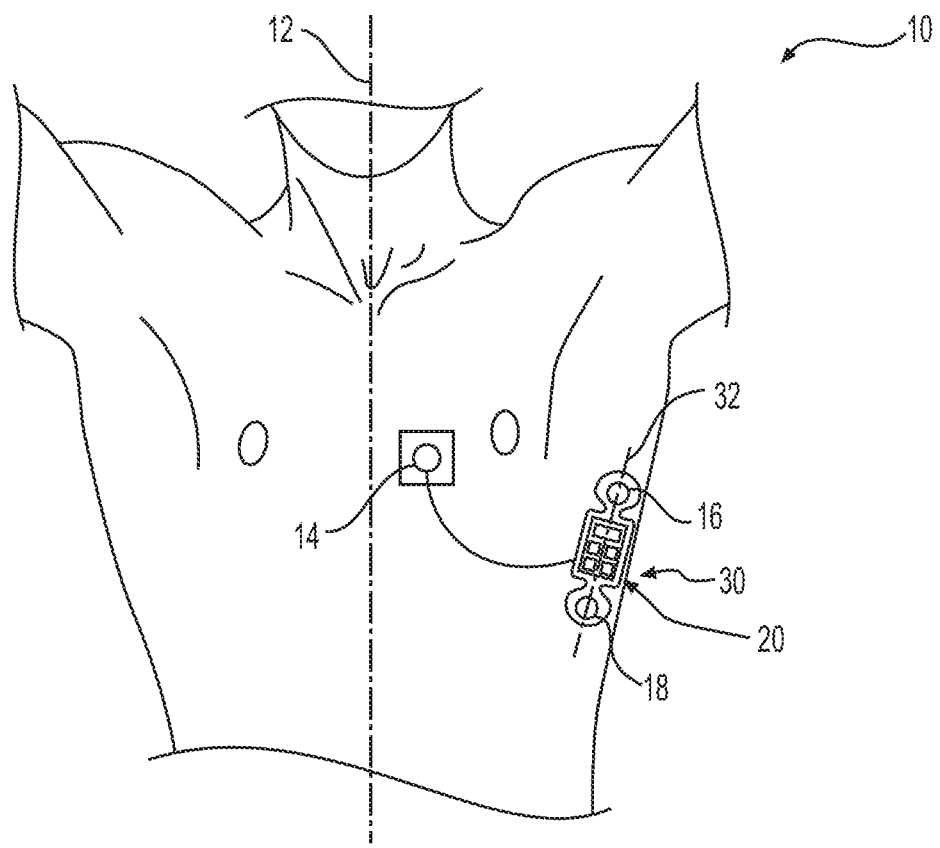
FIG. 3A illustrates a front view of a patient with an exemplary adhesive patch attached.
Figure 3B:
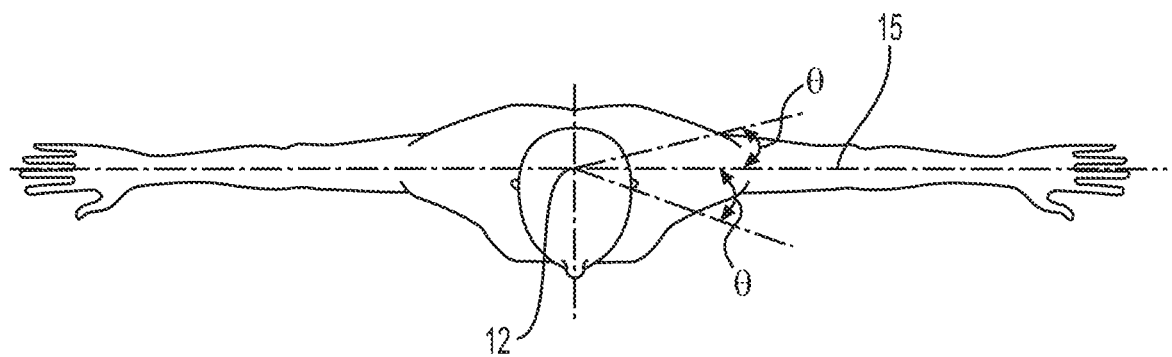
FIG. 3B illustrates a top view of a patient with arms outstretched.

FIG. 3A illustrates an adhesive patch 30 attached to patient 10. FIG. 3A depicts the front view of a patient's thoracic region, and FIG. 3B illustrates a top view of the patient with arms outstretched. In the description that follows, reference will be made to both FIGS. 3A and 3B. Patient 10 may have a vertical axis 12 extending from the patient's head to the patient's feet and a horizontal axis 15, perpendicular to the vertical axis 12, and extending along the patient's outstretched arms. In general, patch 30 may be attached anywhere on the patient's body in any orientation. In some embodiments, adhesive patch 30 is attached to the thoracic region of the patient's torso with its longitudinal axis 32 in a generally vertical orientation (i.e. head-feet). In this orientation, longitudinal axis 32 of patch 30 may be generally aligned with the vertical axis 12 of patient 10. It should be noted that, because of different contours (curved, sloped, etc.) on different regions of the patient's body, general alignment of longitudinal axis 32 with vertical axis 12 (as used herein), does not necessarily mean that the longitudinal axis 32 is parallel to the vertical axis 12. Instead, as illustrated in FIG. 3, the longitudinal axis 32 may extend in the same direction as the vertical axis 12.

Adhesive patch 30 may be attached in a vertical orientation anywhere in the thoracic region of patient 10. As is known to a person of ordinary skill in the art, the thoracic region is the area above the diaphragm and includes the sternal region, the pectoral region, and the axillary region. The sternal region lies over the sternum or the breastbone, the pectoral region includes the region of the chest muscles on either side of the sternum, and the axillary region is the area proximate the armpits. In the exemplary embodiment illustrated in FIG. 3A, patch 30 is attached to a region under the left arm with its longitudinal axis 32 generally aligned with the vertical axis 12. In this disclosure, a region that spans the axillary region and the pectoral region near the axillary region is considered to be under an arm. That is, a region spanning an angle $\theta$ of about 15° on either side of the horizontal axis 15 (see FIG. 3B) extending over the thoracic region is considered to be under an arm.

Electrode 14 may be any type of electrode used in bioelectric signal measurement and may be attached anywhere in the patient's thoracic region. In some embodiments, electrode 14 may be attached at any location where any one of $V_1$ to $V_6$ electrode is commonly positioned during 12 lead ECG measurement. In some embodiments, electrode 14 may be attached to the sternal region or in the left pectoral region proximate the sternal region. In some embodiments, electrode 14 may be positioned at a region above the right atrium of the patient's heart. After attaching the electrode 14 at the desired location, it is connected to the monitor 20. In some embodiments, electrode 14 may be connected to terminal 52 of patch 30 using an external wire.

After the adhesive patch 30 is attached to the patient's skin, the electrodes 16 and 18 are connected to the monitor 20. In embodiments where the monitor 20 is positioned remote from the patch 30, external wires (e.g., from terminals 42, 46) may connect the electrodes 16, 18 to the monitor 20 (see FIG. 1). In other embodiments, the signal from electrodes 16, 18 may be wirelessly transmitted to the monitor 20. In some such embodiments, the measured signals from electrode 14 may be directed to the patch 30 (through terminal 52) and signals from all the electrodes 14, 16, 18 transmitted wirelessly to the monitor 20.

In some embodiments, as illustrated in FIG. 3A, the monitor 20 may be attached to the patch 30. The monitor 20 may be attached to the patch 30 at any location and by any method (adhesive, mechanical fastener, strap, etc.). In some embodiments, the monitor 20 may be detachably clipped (e.g., using a clip) to the central region 35 of patch 30. In some embodiments, a hook and loop system (e.g., Velcro fasteners) may attach monitor 20 to the patch 30. In some embodiments, a strap may couple the monitor 20 to the patch 30. It is also contemplated that, in some embodiments, the patch 30 may have a recess that securely receives the monitor 20 therein. The terminals 42, 46, and 56 may also be connected to the monitor 20 to receive the measured signals from the electrodes 14, 16, 18. In some embodiments, when the monitor 20 is attached to the patch 30, the terminals 42, 46, and 56 of the patch 30 may mate with corresponding terminals of the monitor 20 to direct the signals into the monitor 20.

As described above, these electrode measured signals may be stored, processed, and/or transmitted from the patch 30 to a remote analysis station 60 directly or through an intermediate device. The analysis station 60 may analyze the measured data to identify an anomaly.

Figure 4A:
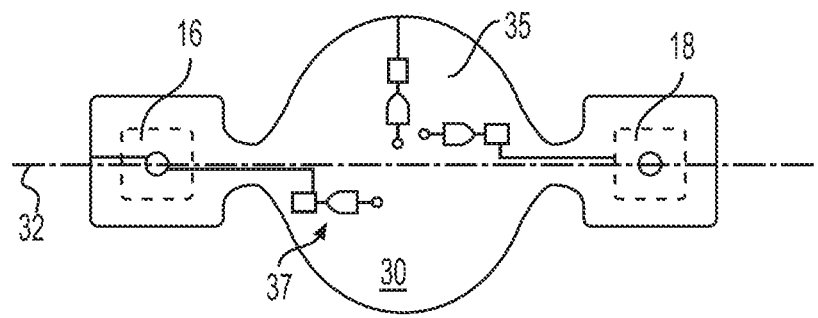
FIGS. 4A-4D illustrate other exemplary embodiments of an adhesive patch which may be used in the ECG measurement system of FIG. 1.

It should be noted that the shape and configuration of the adhesive patch 30 illustrated in FIG. 2A is only exemplary. In general, patch 30 may have any shape suitable for its purpose. FIGS. 4A-4D illustrate some exemplary shapes of patch 30 with two electrodes 16, 18 spaced apart along a longitudinal axis 32. As illustrated in FIG. 4A, in some embodiments, the end portions of the patch 30 may have a generally square or a rectangular configuration and the central region 35 may have a generally circular configuration. The central region 35 may include some circuit elements 37 (filter, A/D converter, etc.) formed thereon to at least partially process the measured bioelectric signals from the electrodes 16, 18. These processed signals may be received by a monitor 20 attached to central region 35 or positioned elsewhere on the patient 10.

Figure 4B:
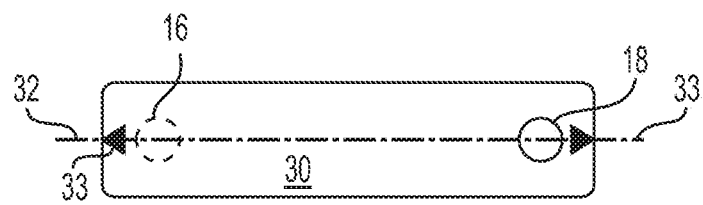
Figure 4C:
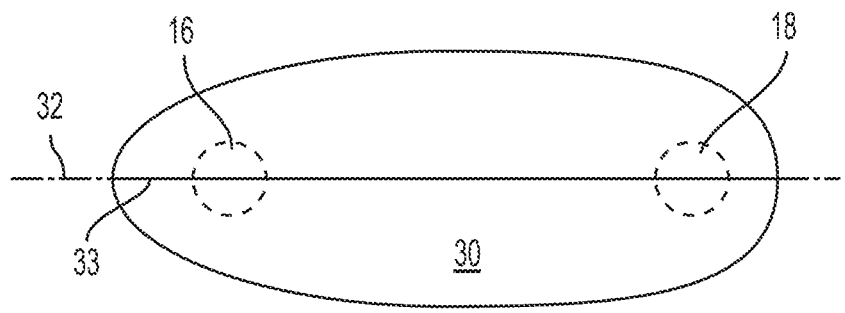
Figure 4D:
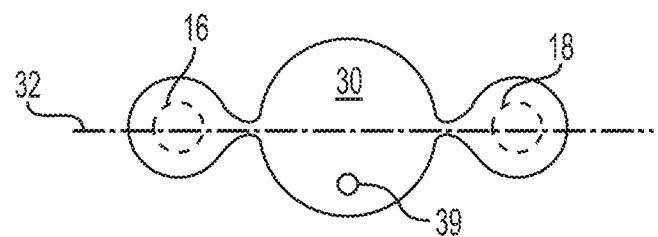

FIG. 4B illustrates an exemplary patch 30 having a generally rectangular shape, and FIG. 4C illustrates an exemplary patch 30 having a generally elliptical shape. As illustrated in FIGS. 4B and 4C, in some embodiments, patch 30 may have markings 33 thereon, for example, arrows or a line. These markings 33 may assist in generally aligning the longitudinal axis 32 of the patch 30 with the vertical axis 12 of the patient 10. FIG. 4D illustrates an exemplary patch 30 in which the end portions and the central region 35 is configured to be substantially circular. As illustrated in FIG. 4D, in some embodiments, patch 30 may include an indicator 39 that alerts the patient 10 when it is time to replace the patch 30. For example, indicator 39 may change color with time, and the patient may be advised to change the patch 30 when the indicator 39 becomes a particular color (red, etc.).

Adhesive patches 30 may also include other features not described with reference to the figures. For instance, patch 30 may include markings (e.g., to identify the name of the manufacturer) and text to assist (e.g., directions of use) the patient in use of the patch 30. It is also contemplated that other sensors (e.g., temperature sensor, accelerometer, sensor to analyze sweat, etc.) may be incorporated into patch 30. For example, in some embodiments, indicator 39 of FIG. 4D may be a sensor that changes color with temperature, in the presence of a constituent in sweat, etc. It should be noted that while certain features (e.g., markings 33, indicator 39) have been described in connection with various embodiments, it is to be understood that any feature described in conjunction with any embodiment disclosed herein may be used with any other embodiment disclosed herein.

While the current disclosure describes using an adhesive patch for ECG monitoring, it should be understood that the disclosure is not limited thereto. Rather, the principles of the systems and methods described herein may be employed for the measurement of any physiologic data of a patient. Those having ordinary skill in the art and access to the teachings provided herein will recognize additional modifications, applications, embodiments, and substitution of equivalents all fall within the scope of the embodiments described herein.

We claim:

1. A method of measuring bioelectric signals of a user, comprising:
    attaching a patch under the user's arm such that a longitudinal axis of the patch is generally aligned with an axis that extends from the user's head to the user's feet, the patch including a first electrode and a second electrode spaced apart along the longitudinal axis;
    attaching a third electrode to the user's chest, wherein the third electrode is separate from the patch;
    operatively coupling a monitor to the first electrode, second electrode, and the third electrode; and
    measuring bioelectric signals using the monitor.

2. The method of claim 1, further including attaching the monitor to the patch.

3. The method of claim 2, wherein attaching the monitor to the adhesive patch includes attaching the monitor between the first electrode and the second electrode.

4. The method of claim 1, wherein attaching the patch under the user's arm includes attaching the patch to the user's thoracic region in an area spanning about 15o on either side of a linear axis that extends through the user's outstretched arms.

5. The method of claim 1, wherein attaching the third electrode includes attaching the third electrode above a right atrium of the user's heart.

6. The method of claim 1, further including transmitting at least a portion of the measured bioelectric signals from the monitor to a remote device.

7. The method of claim 1, wherein the measuring bioelectric signals includes measuring ECG signals.

8. The method of claim 1, further including storing at least a portion of the measured bioelectric signals in the monitor.

* * * * *